United States Patent [19]
Jensen et al.

[11] Patent Number: 6,043,214
[45] Date of Patent: Mar. 28, 2000

[54] METHOD FOR PRODUCING POWDER FORMULATION COMPRISING AN INSULIN

[75] Inventors: Steen Jensen, Dragør; Philip Hansen, Holte, both of Denmark

[73] Assignee: Novo Nordisk A/S, Bagsvaerd, Denmark

[21] Appl. No.: 09/045,397

[22] Filed: Mar. 20, 1998

Related U.S. Application Data

[60] Provisional application No. 60/041,644, Mar. 27, 1997.

[30] Foreign Application Priority Data

Mar. 20, 1997 [DK] Denmark ................................. 0318/97

[51] Int. Cl.⁷ .................................................. A61K 38/28
[52] U.S. Cl. ................................... 514/3; 514/4; 514/866
[58] Field of Search ..................... 514/3, 4, 866

[56] References Cited

U.S. PATENT DOCUMENTS

| | | | |
|---|---|---|---|
| 5,506,203 | 4/1996 | Bäckström et al. | 514/4 |
| 5,747,445 | 5/1998 | Bäckström et al. | 514/4 |

FOREIGN PATENT DOCUMENTS

| | | |
|---|---|---|
| WO 95/00550 | 1/1995 | Denmark . |
| 0692489 A1 | 1/1996 | European Pat. Off. . |
| 9500127 | 1/1995 | WIPO . |
| WO 95/00151 | 1/1995 | WIPO . |
| 9507931 | 3/1995 | WIPO . |
| 9619207 | 6/1996 | WIPO . |

OTHER PUBLICATIONS

Danielson et al. (1994) "New Routes and Means of Insulin Delivery", Childhood and Adolescent Diabetes, Chapman & Hall Medical pp. 571–584.

Niven (1995) "Delivery of Biotherapeutics by Inhalation Aerosol" Critical Reviews in Therapeutic Drug Carrier Systems 12(2&3) :151–231.

Sayani et al. (1996) "Systemic Delivery of Peptides and Proteins" Mucosae Critical Reviews in Therapeutic Drug Carrier Systems 13(1&2) : 85–184.

*Primary Examiner*—Kevin E. Weddington
*Attorney, Agent, or Firm*—Steven T. Zelson, Esq.; Elias J. Lambiris, Esq.

[57] ABSTRACT

The present invention relates to a process for producing a therapeutic powder formulation, comprising (a) providing an acidic aqueous solution comprising an insulin or analoguc or derivative thereof and an enhancer; (b) adjusting the pH to a pH in the range of 4.5 to 7.4; (c) precipitating a product comprising the insulin or analogue or derivative thereof and the enhancer, wherein the precipitation is performed essentially without evaporation of the solution; and (d) removing the water.

31 Claims, No Drawings

METHOD FOR PRODUCING POWDER FORMULATION COMPRISING AN INSULIN

CROSS-REFERENCE TO RELATED APPLICATIONS

This application and claims priority under 35 U.S.C. 119 of Danish application serial no. 0318/97 filed Mar. 20, 1997, and U.S. provisional application Ser. No. 60/041,644 filed on Mar. 27, 1997, the contents of which are fully incorporated herein by reference.

FIELD OF THE INVENTION

The present invention relates to a process for the preparation of a therapeutic powder formulation comprising particles composed of insulin or an analogue or derivative thereof and an enhancer which enhances the absorption of insulin in the lower respiratory tract.

BACKGROUND OF THE INVENTION

Diabetes is a general term for disorders in man having excessive urine excretion as in diabetes mellitus and diabetes insipidus. Diabetes mellitus is a metabolic disorder in which the ability to utilize glucose is more or less completely lost. About 2% of all people suffer from diabetes.

Since the introduction of insulin in the 1920's, continuous strides have been made to improve the treatment of diabetes mellitus. To help avoid extreme glycaemia levels, diabetic patients often practice multiple injection therapy, whereby insulin is administered with each meal.

In the treatment of diabetes mellitus, many varieties of insulin preparations have been suggested and used, such as regular insulin, Semilente® insulin isophane insulin, insulin zinc suspensions, protamine zinc insulin and Ultralente® insulin. Some of the commercial available insulin preparations are characterized by a fast onset of action. Ideally, exogenous insulin is administered at times and in doses that would yield a plasma profile which mimics the plasma profile of endogenous insulin in a normal individual. Insulin preparations containing analogs of human insulin have shown an absorption profile very close to the normal plasma profile, e.g. $Lys^{B28}$-$Pro^{B29}$ human insulin and $Asp^{B28}$ human insulin. However, these new insulin preparations still has to be injected in connection with a meal. In order to circumvent injections, administration of insulin via the pulmonary route could be an alternative elucidating absorption profiles which mimic the endogenous insulin without the need to inject the insulin.

DESCRIPTION OF THE BACKGROUND ART

Administration of insulin via the pulmonary route can be accomplished by either an aqueous solution or a powder preparation. A description of the details can be found in several references, one of the latest being by Niven, Crit. Rev. Ther. Drug Carrier Sys, 12(2&3):151–231 (1995). One aspect covered in said review is the stability issue of protein formulations, aqueous solutions being less stable than powder formulation. So far, all powder formulations have been described as mainly amorphous.

It has been found that when insulin is combined with an appropriate absorption enhancer and is introduced into the lower respiratory tract in the form of a powder of appropriate particle size, it readily enters the systemic circulation by absorption through the layer of epithelial cells in the lower respiratory tract as described in U.S. Pat. No. 5,506,203. The manufacturing process described in said patent, comprising dissolution of insulin at acid pH followed by a pH adjustment to pH 7.4 and addition of sodium taurocholate before drying the solution by a suitable method, results in a powder composed of human insulin and absorption enhancer in a ratio between 9:1 to about 1:1. The powder is characterized as mainly amorphous determined under a polarized light microscope.

DESCRIPTION OF THE INVENTION

Definitions

The expressions "crystalline" and "amorphous" as used herein corresponds to different states of a powder particle, distinguishable by the following method: An aliquot of particles of the powder are mounted in mineral oil on a clean glass slide. Examination using a polarized light microscope elucidates birefringence for crystalline particles.

The expression "enhancer" refers to a substance enhancing the absorption of insulin, insulin analogue or insulin derivative through the layer of epithelial cells lining the alveoli of the lung into the adjacent pulmonary vasculature, i.e. the amount of insulin absorbed into the systemic system is higher than the amount absorbed in the absence of enhancer.

By "analogue of human insulin" (or similar expressions) as used herein is meant human insulin in which one or more amino acids have been deleted and/or replaced by other amino acids, including non-codeable amino acids, or human insulin comprising additional amino acids, i.e. more than 51 amino acids.

By "derivative of human insulin" (or similar expressions) as used herein is meant human insulin or an analogue thereof in which at least one organic substituent is bound to one or more of the amino acids.

In the present context the expression "powder" refers to a collection of essentially dry particles, i.e. the moisture content being below about 10% by weight, preferably below 6% by weight, and most preferably below 4% by weight.

According to the invention it has surprisingly been found that it is possible to obtain particles composed of both insulin and enhancer despite the fact that enhancers and particularly surface active agents normally inhibits precipitation.

Thus, the present invention relates to a process for the preparation of a therapeutic powder formulation comprising particles composed of insulin or an analogue or derivative thereof and an enhancer which enhances the absorption of insulin in the lower respiratory tract, comprising the steps of:

a) providing an acidic aqueous solution comprising insulin or an analogue or derivative thereof, an enhancer and optionally zinc;
b) adjusting the pH value to 4.5 to 7.4, preferably 4.5 to 7, more preferably 4.5 to 6.5, still more preferably 5.5 to 6.2, most preferably 5.5 to 6.1;
c) precipitating a product comprising insulin or an analogue or derivative thereof, an enhancer and optionally zinc; and
d) removing the water.

The process of the invention results in a powder formulation of insulin and enhancer which elucidates a better stability profile than powders of essentially the same composition prepared by spray drying, freeze-drying, vacuum drying and open drying. By this means it is possible to store the powder formulations of the present invention at room temperature in contrary to human insulin preparations for injections and some amorphous insulin powders without stabilizing agent which have to be stored between 2° C. to 8° C.

Furthermore, the obtained powder formulations elucidates better flowing properties than corresponding powder formulations disclosed in the prior art.

The enhancer is advantageously a surfactant, preferably selected from the group consisting of salts of fatty acids, bile salts or phospholipids, more preferably a bile salt.

Preferred fatty acids salts are salts of $C_{10-14}$ fatty acids, such as sodium caprate, sodium laurate and sodium myristate.

Lysophosphatidylcholine is a preferred phospholipid.

Preferred bile salts are salts of ursodeoxycholate, taurocholate, glycocholate and taurodihydrofusidate. Still more preferred are powder formulations according to the invention wherein the enhancer is a salt of taurocholate, preferably sodium taurocholate.

The preferred analogues of human insulin are fast-acting insulin analogues, in particular analogues wherein position B28 is Asp, Lys, Leu, Val or Ala and position B29 is Lys or Pro; or des(B28–B30), des(B27) or des(B30) human insulin. The most preferred analogues are $Asp^{B28}$ human insulin or $Lys^{B28}Pro^{B29}$ human insulin.

The preferred derivatives of human insulin are derivatives comprising one or more lipophilic substituents. The preferred lipophilic insulins are acylated insulins such as those described in WO 95/07931, e.g. human insulin derivatives wherein the $\epsilon$-amino group of $Lys^{B29}$ contains an acyl substituent which comprises at least 6 carbon atoms.

The insulin derivative is most preferably selected from the group consisting of B29-$N^\epsilon$-myristoyl-des(B30) human insulin, B29-$N^\epsilon$-palmitoyl-des(B30) human insulin, B29-$N^\epsilon$-myristoyl human insulin, B29-$N^\epsilon$-palmitoyl human insulin, B28-$N^\epsilon$-myristoyl $Lys^{B28}$ $Pro^{B29}$ human insulin, B28-$N^\epsilon$-palmitoyl $Lys^{B28}Pro^{B29}$ human insulin, B30-$N^\epsilon$-myristoyl-$Thr^{B29}Lys^{B30}$ human insulin, B30-$N^\epsilon$-palmitoyl-$Thr^{B29}Lys^{B30}$ human insulin, B29-$N^\epsilon$-(N-palmitoyl-$\gamma$-glutamyl)-des(B30) human insulin, B29-$N^\epsilon$-(N-lithocholyl-$\gamma$-glutamyl)-des(B30) human insulin, B29-$N^\epsilon$-($\omega$-carboxyheptadecanoyl)-des(B30) human insulin and B29-$N^\epsilon$-($\omega$-carboxyheptadecanoyl) human insulin.

In a preferred embodiment the powder formulation of the present invention comprises an insulin derivative as well as human insulin or an analogue thereof.

However, human insulin is the most preferred insulin to be used in the formulation of the present invention.

In a particular embodiment of the present invention the solution of step a) further comprises zinc, preferably in an amount corresponding to 2 Zn atoms/insulin hexamer to 12 Zn atoms/insulin hexamer, more preferably 2 Zn atoms/insulin hexamer to 10 Zn atoms/insulin hexamer or 4 Zn atoms/insulin hexamer to 12 Zn atoms/insulin hexamer, still more preferably 2 Zn atoms/insulin hexamer to 5 Zn atoms/insulin hexamer.

Particular good results are obtained when the precipitation in step c) is performed by mixing insulin and the enhancer before adding the preferred amount of zinc. Moreover, particular good results are obtained when the precipitation in step c) is performed essentially without evaporation of the solution.

Furthermore, step c) is preferably carried out keeping the preparation at rest but essentially the same result is obtained under slight agitation.

In the process of the invention, the temperature during precipitation is preferably kept in the range of 0° C. to 32° C., preferably 20° C. to 32° C.

The employed molar ratio of insulin to enhancer is preferably 9:1 to 1:9, more preferably between 5:1 to 1:5, and still more preferably between 3:1 to 1:3.

The acidic solution of step a) preferably has a pH value in the range of 3.0–3.9.

In a preferred embodiment the solution of step a) contains a phenolic compound, preferably in an amount corresponding to at least 3 molecules of a phenolic compound/insulin hexamer. The phenolic compound is preferably m-cresol or phenol, or a mixture thereof.

The process of the invention is preferably carried out so as to obtain a substantially crystalline product, i.e. a product in which at least 50% by weight, preferably at least 75% by weight, more preferably at least 90% by weight, of the particles are crystalline.

The powder formulations obtained by the process of the present invention may optionally be combined with a carrier or excipient generally accepted as suitable for pulmonary administration. The purpose of adding a carrier or excipient may be as a bulking agent, stabilizing agent or an agent improving the flowing properties.

Suitable carrier agents include 1) carbohydrates, e.g. monosaccharides such as fructose, galactose, glucose, sorbose, and the like; 2) disaccharides, such as lactose, trehalose and the like; 3) polysaccharides, such as raffinose, maltodextrins, dextrans, and the like; 4) alditols, such as mannitol, xylitol, and the like; 5) inorganic salts, such as sodium chloride, and the like; 6) organic salt, such as sodium citrate, sodium ascorbate, and the like. A preferred group of carriers includes trehalose, raffinose, mannitol, sorbitol, xylitol, inositol, sucrose, sodium chloride and sodium citrate.

This invention is further illustrated by the following examples which, however, are not to be construed as limiting.

EXAMPLE I 625.9 mg human insulin was dissolved in water by adding 2N HCl resulting in a pH=3.6–3.7. 125 µL 4% Zinc chloride solution was added to the insulin solution while mixing. Water was added to 25 mL. 1 g sodium taurocholate was dissolved in 10 mL water. To 16 mL of the insulin solution was then added 4 mL of the taurocholate solution while mixing. Water ad 100 mL was finally added while mixing. The preparation with the spontaneous amorphous precipitate was divided in 7 beakers with 10 mL in each. The pH was adjusted to 4.5, 5.0, 5.5, 6.0, 6.1, 6.5, 7.0 and 7.4 while mixing. After standing at rest for approximately 16 hours at 20° C.–25° C., crystals were formed in all preparations.

An aliquot of each preparation elucidates almost complete crystalline state of the particles as determined under a polarized light microscope. The size of the individual crystals was determined to 1 µm–5 µm.

The supernatant was carefully removed from each of the preparations and the remaining wet crystalline fraction was dried by placing in a vacuumdryer for approximately 5 hours.

The dry insulin powders were analyzed by RP-HPLC for the content of human insulin and sodium taurocholate and the results showed a proportion of human insulin and sodium taurocholate of 3:1 to 7:1 depending on the actual pH value.

EXAMPLE II 625.9 mg human insulin was dissolved in water by adding 2N HCl resulting in a pH=3.6–3.7. Water was added to 25 mL. 1 g sodium taurocholate was dissolved in 10 mL water. The insulin solution was divided in 6 beakers with 4 mL in each. A 0.4% Zinc chloride solution was added to the insulin solutions while mixing in an increasing amount: 81 µL, 123 µL, 164 µL, 205 µL, 285 µL and 410 µL. To each of the solutions were then added 1 mL of the taurocholate solution while mixing. Water ad 25 mL was finally added while mixing. The pH was adjusted to 6.1 while mixing. Spontaneously, an amorphous precipitate was formed in each of the preparations. After standing at rest for approximately 16 hours at 20° C.–25° C., crystals were formed in all preparations.

An aliquot of each preparation elucidates almost complete crystalline state of the particles as determined under a polarized light microscope. The size of the individual crystals was determined to 1µ–5µ.

The supernatant was carefully removed from each of the preparations and the remaining wet crystalline fraction was dried by placing in a vacuumdryer for approximately 5 hours.

The dry insulin powders were analyzed by RP-HPLC for the content of human insulin and sodium taurocholate and the results showed a proportion of human insulin and sodium taurocholate of 4:1 to 5:1 depending on the content of zinc.

EXAMPLE III 625,3 mg human insulin was dissolved in water by adding 2N HCl resulting in a pH=3.6–3.7. 125 µL 4% Zinc chloride solution was added to the insulin solution while mixing. Water was added to 25 mL. 1 g sodium taurocholate was dissolved in 10 mL water. The insulin solution was divided in 4 beakers with 1.6 mL in each. To each of the beakers were added 400 µL of taurocholate solution while mixing. A sodium chloride solution (100 mg/mL) was added while mixing in an increasing amount: 0 µL, 58 µL, 116 µL and 232 µL. Water ad 10 mL was finally added while mixing. The pH was adjusted to 6.1 while mixing. An aliquot of each preparation elucidates 50% to 80% crystalline state of the particles as determined under a polarized light microscope. The size of the individual crystals was determined to 1µ–5µ.

The dry insulin powders were analyzed for the content of human insulin and sodium taurocholate and the results showed a proportion of human insulin and sodium taurocholate of 3:1 in all the preparations

EXAMPLE IV 2.5 g human insulin was dissolved in water by adding 2N HCl resulting in a pH=3.6–3.7. 500 µL 4% Zinc chloride solution was added to the insulin solution while mixing. Water was added to 100 mL. 2.5 g sodium taurocholate was dissolved in 25 mL water. The insulin solution was divided in 9 beakers with 8 mL in each. To 3 insulin solutions (group 1) were added 2 mL, to the next 3 insulin solutions (group 2) were added 2.25 mL and to the last 3 insulin solutions (group 3) were added 2.50 mL of the taurocholate solution while mixing. In each of the 3 groups, a sodium chloride solution (100 mg/mL) was added in increasing amounts: 0 µL, 290 µL and 1160 µL. Water ad 50 mL was finally added while mixing. The pH was adjusted to 6.1 while mixing. Spontaneously, an amorphous precipitate was formed in each of the preparations. After standing at rest for approximately 16 hours at 20° C.–25° C., crystals were formed in all preparations.

An aliquot of each preparation elucidates almost complete crystalline state of the particles with no sodium chloride added while the preparations with sodium chloride elucidate approximately 50% to 80% crystalline state as determined under a polarized light microscope. The size of the individual crystals was determined to 1µ–5µ.

The supernatant was carefully removed from each of the preparations and the remaining wet crystalline fraction was dried by placing in a vacuum dryer for approximately 5 hours.

The dry insulin powders were analyzed for the content of human insulin and sodium taurocholate and the results showed a proportion of human insulin and sodium taurocholate of 6:1 to 3:1 in the preparations.

We claim:

1. A process for the preparation of a therapeutic powder formulation, comprising
    (a) providing an acidic aqueous solution comprising an insulin or analogue or derivative thereof and an enhancer;
    (b) adjusting the pH to a pH in the range of 4.5 to 7.4;
    (c) precipitating a product comprising the insulin or analogue or derivative thereof and the enhancer, wherein the precipitation is performed essentially without evaporation of the solution; and
    (d) removing the water.

2. The process of claim 1, wherein the pH is adjusted in step (b) to a pH in the range of 4.5 to 7.

3. The process of claim 2, wherein the pH is adjusted in step (b) to a pH in the range of 4.5 to 6.5.

4. The process of claim 3, wherein the pH is adjusted in step (b) to a pH in the range of 5.5 to 6.2.

5. The process of claim 4, wherein the pH is adjusted in step (b) to a pH in the range of 5.5 to 6.1.

6. The process of claim 1, wherein the enhancer is a surfactant.

7. The process of claim 6, wherein the surfactant is a salt of a fatty acid, a bile salt or a phospholipid.

8. The process of claim 7, wherein the surfactant is a salt of taurocholate.

9. The process of claim 1, wherein the solution of step (a) further comprises zinc in an amount corresponding to 2 Zn atoms/insulin hexamer to 12 Zn atoms/insulin hexamer.

10. The process of claim 9, wherein the solution of step (a) contains zinc in an amount corresponding to 2–10 Zn atoms per hexamer of the insulin or analogue or derivative thereof.

11. The process of claim 10, wherein the solution of step (a) contains zinc in an amount corresponding to 2–5 Zn atoms per hexamer of the insulin or analogue or derivative thereof.

12. The process of claim 1, wherein the solution of step (a) has a pH in the range of 3.0–3.9.

13. The process of claim 1, wherein the solution of step (a) further comprises a phenolic compound in an amount corresponding to at least 3 molecules of the phenolic compound per hexamer of the insulin or analogue or derivative thereof.

14. The process of claim 13, wherein the phenolic compound is m-cresol, phenol, or a mixture thereof.

15. The process of claim 1, wherein the precipitation in step (c) is performed under slight agitation.

16. The process of claim 1, wherein the removal of water in step (d) is carried out using vacuum evaporation.

17. The process of claim 1, which further comprises micronizing the product of step (d).

18. The process of claim 1, wherein the temperature during precipitation is kept in the range of 0° C. to 32° C.

19. The process of claim 18, wherein the temperature during precipitation is kept in the range of 20° C. to 32° C.

20. The process of claim 1, wherein the molar ratio of the insulin or analogue or derivative thereof to the enhancer is 9:1 to 1:9.

21. The process of claim 20, wherein the molar ratio of the insulin or analogue or derivative thereof to the enhancer is 5:1 to 1:5.

22. The process of claim 21, wherein the molar ratio of the insulin or analogue or derivative thereof to the enhancer is 3:1 to 1:3.

23. The process of claim 1, wherein the insulin or analogue or derivative thereof is human insulin wherein the amino acid at position B28 is Asp, Lys, Leu, Val or Ala and the amino acid at position B29 is Lys or Pro; or des (B28–B30), des(B27) or des(B30) human insulin.

24. The process of claim 23, wherein the insulin or analogue or derivative thereof is $Asp^{B28}$ human insulin or $Lys^{B28}Pro^{B29}$ human insulin.

25. The process of claim 1, wherein the insulin or analogue or derivative thereof is human insulin wherein the ε-amino group of $Lys^{B29}$ contains an acyl substituent which comprises at least 6 carbon atoms.

26. The process of claim 1, wherein the insulin or analogue or derivative thereof is selected from the group consisting of B29-$N^{\epsilon}$-myristoyl-des(B30) human insulin, B29-$N^{\epsilon}$-palmitoyl-des(B30) human insulin, B29-$N^{\epsilon}$-myristoyl human insulin, B29-$N^{\epsilon}$-palmitoyl human insulin, B28-$N^{\epsilon}$-myristoyl $Lys^{B28}Pro^{B29}$ human insulin, B28-$N^{\epsilon}$-palmitoyl $Lys^{B28}$ $Pro^{B29}$ human insulin, B30-$N^{\epsilon}$-myristoyl-$Thr^{B29}Lys^{B30}$ human insulin, B30-$N^{\epsilon}$-palmitoyl-$Thr^{B29}Lys^{B30}$ human insulin, B29-$N^{\epsilon}$-(N-palmitoyl-γ-glutamyl)-des(B30) human insulin, B29-$N^{\epsilon}$-(N-lithocholyl-γ-glutamyl)-des(B30) human insulin, B29-$N^{\epsilon}$-(ωcarboxyheptadecanoyl)-des(B30) human insulin and B29-$N^{\epsilon}$-(ω-carboxyheptadecanoyl) human insulin.

27. The process of claim 1, wherein at least 50% by weight of the particles of the product are crystalline.

28. The process of claim 27, wherein at least 75% by weight of the particles of the product are crystalline.

29. The process of claim 28, wherein at least 90% by weight of the particles of the product are crystalline.

30. A therapeutic powder formulation produced by a process of claim 1.

31. A method of treating diabetes, comprising administering to a subject in need thereof a therapeutically effective amount of the powder formulation of claim 30.

* * * * *